United States Patent [19]
Edvardsson et al.

[11] Patent Number: 5,885,623
[45] Date of Patent: Mar. 23, 1999

[54] ARRANGEMENT FOR AIR-LAYER FIBRE BODIES ON A MOVING AIR-PERMEABLE CONVEYOR PATH

[75] Inventors: Gunnar Edvardsson, Bohus-Björkö ; Claes Göransson, Landvetter, both of Sweden

[73] Assignee: SCA Hygiene Products AB, Gothenburg, Sweden

[21] Appl. No.: 817,884

[22] PCT Filed: Nov. 6, 1995

[86] PCT No.: PCT/SE95/01311

§ 371 Date: May 1, 1997

§ 102(e) Date: May 1, 1997

[87] PCT Pub. No.: WO96/14458

PCT Pub. Date: May 17, 1996

[30] Foreign Application Priority Data

Nov. 7, 1994 [SE] Sweden ................................. 9403811

[51] Int. Cl.$^6$ ....................................................... D04H 1/72
[52] U.S. Cl. ........................... 425/81.1; 19/302; 264/113; 264/518
[58] Field of Search ................................ 425/81.1, 82.1; 264/517, 518, 113; 19/302

[56] References Cited

U.S. PATENT DOCUMENTS

| | | | |
|---|---|---|---|
| 4,904,440 | 2/1990 | Angstadt | 425/81.1 |
| 5,004,579 | 4/1991 | Wislinski et al. | 425/81.1 |
| 5,064,484 | 11/1991 | Craig et al. | 425/81.1 |

FOREIGN PATENT DOCUMENTS

| | | |
|---|---|---|
| 0 060 949 | 9/1982 | European Pat. Off. . |
| 0 399 511 | 11/1990 | European Pat. Off. . |
| 0 453 892 | 10/1991 | European Pat. Off. . |
| 2 124 264 | 2/1984 | United Kingdom . |
| 2 191 794 | 12/1987 | United Kingdom . |
| WO 95/22656 | 8/1995 | WIPO . |

Primary Examiner—Patrick Ryan
Assistant Examiner—Joseph Leyson
Attorney, Agent, or Firm—Young & Thompson

[57] ABSTRACT

An arrangement for fibre-laying on a moving air-permeable conveyor path (2) fibre bodies which are comprised of at least two different layers. The arrangement includes for each fibre layer a succession of air-laying units disposed sequentially in the direction of movement of the conveyor path, wherein each of the units includes elements (6, 7) for passing a stream of air-borne fibres to a region above the moving conveyor path (2), elements (3, 4) for generating a subpressure beneath the air-permeable conveyor path in the proximity of the region in which the stream of air-borne fibres is delivered, and elements (6, 7) for shielding the stream of air-borne fibres from ambient air. According to the invention a transition region (1) into which ambient air can freely enter is provided between each of pair elements (6, 7) arranged sequentially in the direction of movement, such as to delimit a stream of air-borne fibres, and the elements (3, 4) which generate a subpressure beneath the air-permeable conveyor path extend beyond the fibre stream limiting elements and into the transition region.

6 Claims, 1 Drawing Sheet

ARRANGEMENT FOR AIR-LAYER FIBRE BODIES ON A MOVING AIR-PERMEABLE CONVEYOR PATH

FIELD OF THE INVENTION

The present invention relates to an arrangement for fibre-laying on a moving air-permeable conveyor path fibre bodies which are comprised of at least two different layers, wherein the arrangement includes for each fibre layer air-laying units which are arranged mutually sequentially in the movement direction of the conveyor path, wherein each such unit includes means for delivering a stream of air-borne fibres to a region above the moving conveyor path, means for generating a subpressure beneath the air-permeable conveyor path in the delivery region of the stream of air-borne fibres, and means for shielding the stream of air-borne fibres from ambient air.

BACKGROUND OF THE INVENTION

Such arrangements are often used to form the absorbent bodies included in diapers, sanitary napkins, incontinence guards and like products, and the bodies often include more than one layer. One problem encountered when air-laying a fibre layer on top of an earlier laid layer is that because of the pressure difference between the interior of the mat-forming hoods which delimit the flows of air-borne fibres, air currents occur at the edges of the hoods, these air streams or air currents having a transversal direction relative to the air-borne fibres and are able to damage or destroy the earlier laid layer. EP-B1-0,292,624 teaches a solution to this problem. This prior document describes two mat-forming hoods which are mounted one immediately after the other, and two vacuum boxes which coact with the hoods. In order to avoid a difference in pressure at the join between the two hoods, the vacuum box of one hood extends beneath the other hood. One drawback with this solution is that the air-laying of fibres beneath one hood is effected under the influence of the subpressure that prevails in two different vacuum boxes, which results in inhomogeneities in the formed layer, and the stream of air-borne fibres is disturbed as a result of the pressure difference occurring in the hood. Another drawback is that the hoods are joined together via a relatively broad gap which equalizes the pressure difference between the hoods in the region of the join.

An object of the present invention is to solve the aforesaid problems in a manner which does not encumber the solution with the drawbacks of the known arrangement.

SUMMARY OF THE INVENTION

This object is achieved in accordance with the invention by means of an arrangement of the kind defined in the introduction which is characterized in that between each pair of means arranged mutually sequentially in the movement direction and delimiting a stream of air-borne fibres there is provided a transition or bridging region into which ambient air can enter freely; and in that the means which generate a subpressure beneath the air-permeable conveyor path extend beyond the fibre-stream delimiting means and into the transition or bridging region. Because the subpressure generating means extend into the transition region, there is formed a local subpressure at the limits of the transition region so that the pressure in the ambient air externally of the stream of air-borne fibres will be locally equal to the pressure in the stream, therewith eliminating the occurrence of transverse air-streams in the intermediate region between hoods and transition regions. Because the fibre layer that passes through the transition region has already been laid, no inhomogeneities will occur in the layer as a result of the influence of the different sub-pressures in the two vacuum boxes.

According to one preferred embodiment of the arrangement in which the moving conveyor path is comprised of a succession of moulds having air-permeable bottoms and disposed around the periphery of a mat-forming drum and in which at least two mat-forming hoods which each coact with an individual vacuum box are mounted peripherally one after the other and radially outside the mat-forming drum, each pair of mat-forming hoods is separated from another circumferentially, so as to provide between the hoods a transition region into which air can enter freely, and the vacuum boxes coacting with the hoods extend into the transition region. The vacuum boxes also extend circumferentially beyond associated mat-forming hoods on all sides thereof.

BRIEF DESCRIPTION OF THE DRAWINGS

The invention will now be described in more detail with reference to the accompanying drawing, in which.

DETAILED DESCRIPTION OF THE INVENTION

Figure 1:
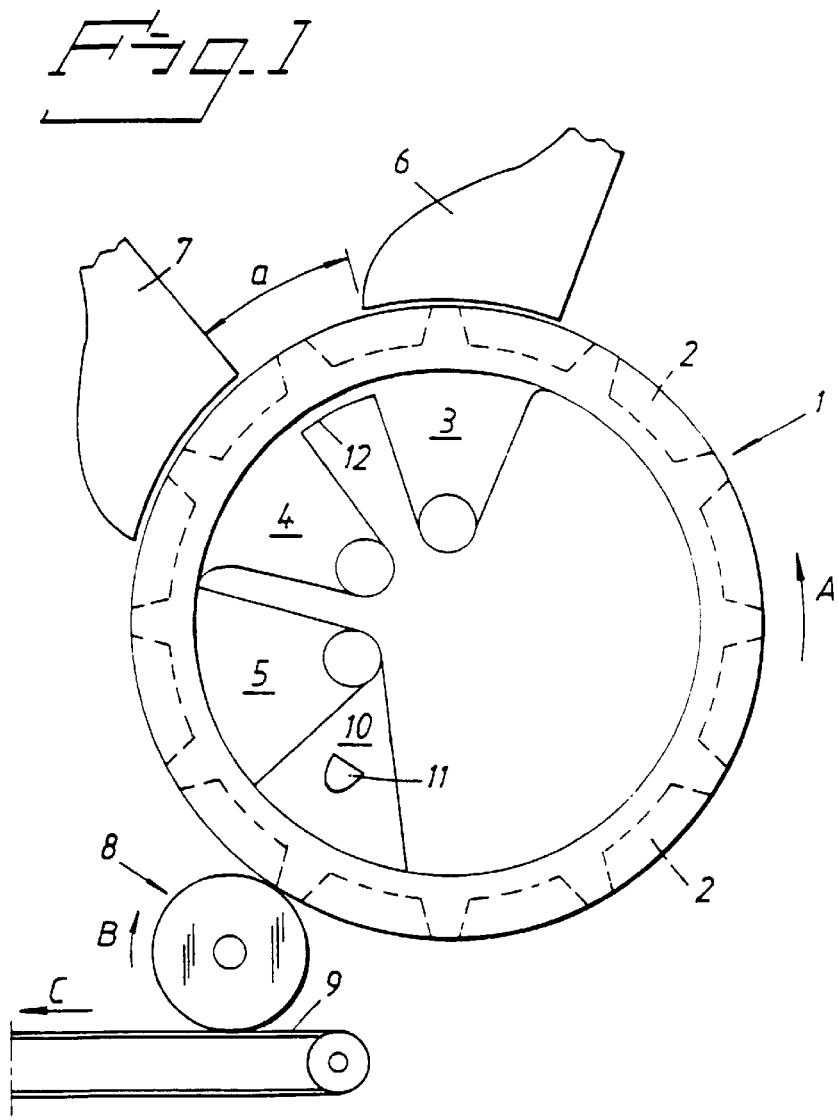
FIG. 1 is a schematic side view of one embodiment of an inventive arrangement.

The arrangement illustrated schematically in the drawing includes a mat-forming drum 1 which rotates in the direction of the arrow A. Arranged peripherally around the drum 1 is a succession of moulds or forms 2 which have air-permeable bottoms. The arrangement also includes three stationary vacuum boxes 3, 4 and 5 which are disposed sequentially and radially inwards of the moulds 2, and two mat-forming hoods 6, 7 which are located radially outside the moulds 2 and coact with the vacuum boxes 3 and 4 respectively. Although not shown, the mat-forming hoods 6, 7 are connected to means for delivering air-borne fibres, for instance air-borne cellulose fluff fibres. When the arrangement is operating, the vacuum boxes 3, 4 coacting with the mat-forming hoods 6, 7 function to draw a stream of air-borne fibres into the moulds 2 as they pass beneath the hoods 6, 7, wherewith the air in which the fibres are suspended passes through the air-permeable bottoms of the moulds while the fibres are captured therein. Thus, as respective moulds pass the hood 6, a first fibre layer is air-laid in the moulds, while a second fibre layer is laid on top of the first fibre layer as the moulds pass the second hood 7.

The illustrated arrangement thus forms a succession of two-layer fibre bodies, which are deposited downstream of the mat-forming hood 7 onto a transfer wheel 8 which, in turn, deposits the formed bodies onto a conveyor 9. The direction of rotation of the transfer wheel and the running direction of the conveyor are indicated in FIG. 1 by respective arrows B and C. The vacuum box 5 has the sole function of retaining the fibre bodies in the moulds 2 as the bodies are transported from the hood 7 to the transfer wheel 8, and the subpressure in the vacuum box is relatively small. The arrangement illustrated in FIG. 1 also includes a blow chamber 10 having a blow nozzle 11 by means of which the fibre bodies are blown from the moulds 2. Although not shown, the transfer wheel 8 includes a vacuum box which functions to hold the transferred fibre bodies firmly. It is possible to exclude the blow chamber 10 and to rely solely on the subpressure generated in the latter vacuum box to extract the fibre bodies from the moulds 2.

Figure 2:
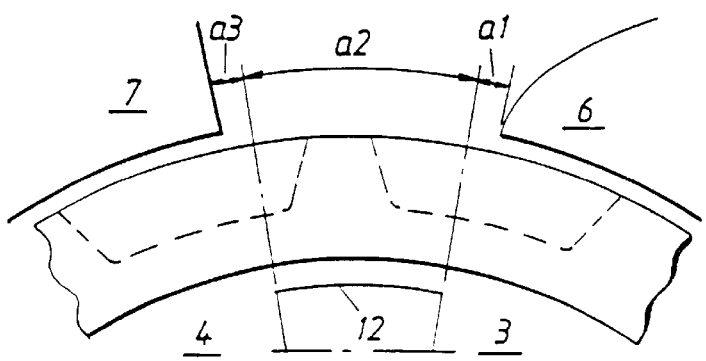
FIG. 2 illustrates a section of the FIG. 1 in larger scale.

According to the invention, the hoods 6 and 7 are mutually separated in the circumferential direction of the drum 1 by a transition region a which extends between the downstream edge of the hood 6 and the upstream edge of the hood 7. The vacuum boxes 3, 4 on the other hand are joined mutually by a narrow gap that extends between a partition wall 12 and the peripheral surface of the mat-forming drum. The vacuum boxes 3 and 4 also extend into the transition region a, so that the extension of the downstream edge of the vacuum box 3 will be located at a distance a1 from the downstream edge of the hood 6, and the extension of the upstream edge of the vacuum box 4 will be spaced at a distance a3 from the downstream edge of the hood 7, as shown in FIG. 2. Because the vacuum boxes 3 and 4 extend into the transition region, the pressures that prevail on respective sides of the downstream edge of the hood 6 and the upstream edge of the hood 7 will be generally equal, thereby causing a generally radial air flow to pass through the moulds 2 in the gaps between the hood edges and the extensions of the vacuum box edges. Consequently, no air will flow transversely into the hoods 6 or 7 as a result of a pressure difference. Each of the vacuum boxes 3 and 4 will preferably extend slightly outside the downstream edge and side edges and the upstream edge and side edges of respective hoods 6 and 7, so as to ensure that the flow or stream of air-borne fibres in respective hoods will take place in the absence of disturbances caused by transverse currents of ambient air. The pressure differences generated between the vacuum boxes 3 and 4 in the narrow gap defined by the wall 12 will be equalized at the same time as a relatively low stream of ambient air is drawn through the first fibre layer air-laid in the mould 2 subsequent to the passage of the mould past the mat-forming hood 6. This low air stream, however, is sufficiently large to ensure that the layer will be held securely in the mould.

Because the fibre layer that is laid first in the moulds 2 is subjected to the pressures prevailing in both vacuum boxes 3, 4 in a transition region into which ambient air can freely enter, there is no risk that the pressure prevailing in the downstream vacuum box 4 will have a disturbing influence on the air-laying of the first fibre layer, or that the pressure prevailing in the upstream vacuum box 3 will have a disturbing influence on the air-laying of the second fibre layer. Because the vacuum boxes 3 and 4 extend into the transition region, it is also ensured that no transverse flows will occur in the hoods. Such transverse flows, or currents, are able to damage the air-laid fibre layers and to disturb the flow of air-borne fibres in the mat-forming hoods.

Although the size of the transition region a is not particularly critical, the distances a1 and a3 will preferably be between 5–40 mm, more preferably 10–30 mm, in order to ensure that no transverse air flows will occur at the edges of the hoods 6, 7. The distance a2 will preferably be greater than 10 mm.

It will be understood that the described embodiment can be modified within the scope of the invention, particularly with regard to the dimensions of the components of the arrangement, the number of moulds, and so on. The vacuum boxes may also be mutually separated by a radial wall which projects out from the partition wall 12, and suitable means may be provided between the downstream mat-forming hood and the transfer wheel for the purpose of scraping or brushing surplus fibre material from the moulds 2. The arrangement may also include more than two mat-forming hoods with a corresponding increase in the number of transition regions, and means for delivering particle material, for instance so-called superabsorbents, may be provided in the transition region or regions, or within the hoods. Superabsorbent particles may also be delivered in the air-borne fibre stream before the stream reaches the mat-forming hoods. In the case of very large pressure differences between vacuum boxes mounted beneath different mat-forming hoods, it may be suitable to provide one or more additional vacuum boxes in the transition region between the vacuum boxes of the hoods, so as to reduce the pressure differences between mutually sequential vacuum boxes in the transition region. It will also be understood that the invention can be applied when air-laying fibre bodies on linearly moving conveyor paths, which may be provided with a succession of moulds or have a flat air-permeable bottom for producing a continuous two-layer or multi-layer material web. The invention is therefore restricted solely by the contents of the following Claims.

What is claimed is:

1. In an arrangement for air-laying on a moving air-permeable conveyor path fibre bodies which are comprised of at least two different layers, wherein the arrangement includes for each fibre layer a succession of air-laying units disposed sequentially in the direction of movement of the conveyor path, each of said units including means for delivering a stream of air-borne fibres to a region above the moving conveyor path, means for each unit for generating a subpressure beneath the air-permeable conveyor path in the proximity of the region in which the stream of air-borne fibres is delivered, and at least a pair of shielding means for shielding the two different streams of air-borne fibres from ambient air and for delimiting the streams, the improvement wherein a transition region into which ambient air can freely enter is provided and extends between each pair of shielding means arranged sequentially in the direction of movement; and each means which generates a subpressure beneath the air-permeable conveyor path extends beyond the delimited stream of air-borne fibres and into the transition region.

2. The arrangement according to claim 1, wherein each means for generating a subpressure beneath the air-permeable conveyor path extends 5–40 mm into the transition region.

3. The arrangement according to claim 2, wherein each means for generating a subpressure beneath the air-permeable conveyor path extends 10–30 mm into the transition region.

4. The arrangement according to claim 1, wherein the moving conveyor path comprises a succession of moulds having air-permeable bottoms and disposed around the periphery of a mat-forming drum, at least a pair of mat-forming hoods being disposed sequentially around the drum periphery and externally thereof, each of said mat-forming hoods coacting with a respective vacuum box, the hoods of each pair of mat-forming hoods being mutually separated circumferentially so as to provide between the hoods said transition region into which ambient air can enter freely; and the vacuum boxes, which coact with the mat-forming hoods, extending into the transition region.

5. The arrangement according to claim 4, wherein the vacuum boxes coacting with the mat-forming hoods are mutually joined in the transition region by a narrow gap which extends between the drum and mutually opposing edges of the vacuum boxes in the circumferential direction.

6. The arrangement according to claim 4, wherein the vacuum boxes extend beyond associated mat-forming hoods in the circumferential direction, on all sides of said associated hood.

* * * * *